United States Patent
Jobson et al.

(10) Patent No.: US 7,189,377 B1
(45) Date of Patent: Mar. 13, 2007

(54) APPARATUS FOR PERFORMING INTEGRATED PROCESS FOR REPRODUCTION OF VINYL ACETATE AND/OR ACETIC ACID USING A FLUIDIZED BED

(75) Inventors: Simon Jobson, Hornsea (GB); Derrick John Watson, Hornsea (GB)

(73) Assignee: BP Chemicals Limited, London (GB)

( * ) Notice: Subject to any disclaimer, the term of this patent is extended or adjusted under 35 U.S.C. 154(b) by 874 days.

(21) Appl. No.: 09/626,157

(22) Filed: Jul. 26, 2000

Related U.S. Application Data

(60) Division of application No. 09/461,097, filed on Dec. 14, 1999, which is a continuation of application No. 09/055,398, filed on Apr. 6, 1998, now Pat. No. 6,040,474, which is a continuation of application No. PCT/GB97/02101, filed on Feb. 5, 1997.

(30) Foreign Application Priority Data

Aug. 7, 1996 (GB) ................................ 9616573.3

(51) Int. Cl.
*B01J 10/00* (2006.01)
(52) U.S. Cl. ...................... 422/188; 422/189; 422/236; 422/139; 422/190; 422/211; 560/231; 560/243; 560/261; 560/548; 562/548; 202/173; 202/204; 202/172
(58) Field of Classification Search ................ 422/188, 422/189, 236, 139, 190, 211; 560/243, 231, 560/261, 548; 562/548; 202/173, 204, 172; 203/71
See application file for complete search history.

(56) References Cited

U.S. PATENT DOCUMENTS

| | | | | |
|---|---|---|---|---|
| 3,404,175 A | * | 10/1968 | Mercier | 560/231 |
| 3,557,191 A | * | 1/1971 | Copelin | 560/243 |
| 3,641,121 A | * | 2/1972 | Swift | 560/243 |
| 3,758,666 A | * | 9/1973 | Frevel et al. | 423/247 |
| 3,862,216 A | * | 1/1975 | Calcagno et al. | 560/243 |
| 3,914,377 A | * | 10/1975 | Anderson et al. | 423/213.7 |
| 4,353,783 A | * | 10/1982 | Roscher et al. | 203/14 |
| 4,934,519 A | * | 6/1990 | Wolf et al. | 203/96 |
| 5,162,578 A | * | 11/1992 | McCain et al. | 562/512.2 |
| 5,348,707 A | * | 9/1994 | Harandi et al. | 422/129 |
| 5,821,384 A | | 10/1998 | Zoeller et al. | |
| 6,143,921 A | | 11/2000 | Karim et al. | |

FOREIGN PATENT DOCUMENTS

| | | |
|---|---|---|
| EP | 0028362 A2 | 5/1981 |
| GB | 1 010 068 | 11/1965 |
| GB | 1 209 727 | 10/1970 |

OTHER PUBLICATIONS

Anonymous: 33830—Chemical Process Research Disclosure, No. 338, Jun. 1992, Emsworth, pp. 445-447.
Handbook of Chemistry and Physics, 55th Ed., Weast, Editor, pp. D2 and D35 (1974).
ECN 11-17, Mar. 1996, p. 17.

* cited by examiner

*Primary Examiner*—Glenn Caldarola
*Assistant Examiner*—Alexis Wachtel
(74) *Attorney, Agent, or Firm*—Nixon & Vanderhye

(57) ABSTRACT

1. Acetic acid and/or vinyl acetate are produced by an integrated process which comprises the steps:—
(a) contacting in a first reaction zone a gaseous feedstock comprising ethylene and/or ethane and optionally steam with a molecular oxygen-containing gas in the presence of a catalyst active for the oxidation of ethylene to acetic acid and/or ethane to acetic acid and ethylene to produce a first product stream comprising acetic acid, water and ethylene (either as unreacted ethylene and/or as co-produced ethylene) and optionally also ethane, carbon monoxide, carbon dioxide and/or nitrogen;

(b) contacting in a second reaction zone in the presence or absence of additional ethylene and/or acetic acid at least a portion of the first gaseous product stream comprising at least acetic acid and ethylene and optionally also one or more of water, ethane, carbon monoxide, carbon dioxide and/or nitrogen with a molecular oxygen-containing gas in the presence of a catalyst active for the production of vinyl acetate to produce a second product stream comprising vinyl acetate, water, acetic acid and optionally ethylene;

(c) separating the product stream from step (b) by distillation into an overhead azeotrope fraction comprising vinyl acetate and water and a base fraction comprising acetic acid;

(d) either (i) recovering acetic acid from the base fraction separated in step (c) and optionally recycling the azeotrope fraction separated in step (c) after partial or complete separation of the water therefrom to step (c), or (ii) recovering vinyl acetate from the azeotrope fraction separated in step (c) and optionally recycling the base fraction separated in step (c) to step (b), or (iii) recovering acetic acid from the base fraction separated in step (c) and recovering vinyl acetate from the overhead azeotrope fraction recovered in step (c).

14 Claims, 1 Drawing Sheet

APPARATUS FOR PERFORMING INTEGRATED PROCESS FOR REPRODUCTION OF VINYL ACETATE AND/OR ACETIC ACID USING A FLUIDIZED BED

This application is a division of Ser. No. 09/461,097 filed Dec. 14, 1999, now U.S. Pat No. 6,180,821, which is a continuation of Ser. No. 09/055,398 filed Apr. 6, 1998, now U.S. Pat. No. 6,040,474, which is a continuation of PCT/GB/97/02101 with and international filing date of Aug. 8, 1997.

The present invention relates generally to an integrated process for the production of acetic acid and/or vinyl acetate and in particular to an integrated process for the production of either acetic acid or vinyl acetate or both acetic acid and vinyl acetate in any pre-determined and variable proportions from a gaseous feedstock comprising ethylene and/or ethane.

Acetic acid, useful as a feedstock for the production of vinyl acetate, may be prepared by several methods as commonly practiced in the industry, for example by the liquid phase carbonylation of methanol and/or a reactive derivative thereof in the presence of a Group VIII noble metal catalyst, an alkyl iodide promoter and a finite concentration of water; however this process does not readily lend itself to integration since small quantities of iodide in the acid are known to be poisons for palladium-based vinyl acetate catalysts. Alternatively, acetic acid may be produced by the catalytic oxidation of ethylene and/or ethane. However, this process though attractive from the point of view of integration, suffers from the disadvantage that large quantities of water are produced as a by-product of the process. Moreover, in a preferred method of operation water (steam) is added to the feedstock to improve selectivity. This, and the generated water, requires removal, necessitating expensive product separation.

Vinyl acetate is generally prepared commercially by contacting acetic acid and ethylene with molecular oxygen in the presence of a catalyst active for the production of vinyl acetate. Suitably, the catalyst may comprise palladium, an alkali metal acetate promoter and an optional co-promoter (for example, gold or cadmium) on a catalyst support. Acetic acid produced by carbonylation generally requires extensive purification to remove inter alia iodides arising from the catalyst system generally employed because iodides are recognised as potential vinyl acetate catalyst poisoners. The ethylene feedstock generally requires purification to remove inert hydrocarbons such as ethane present in cracker products. Alternatively, the process for the production of vinyl acetate requires a costly purge to remove the accumulated hydrocarbons.

Combinations of processes for producing vinyl acetate are known in the art. Thus, GB-A-1,139,210 discloses a vapour phase process for the production of unsaturated organic esters from a feed mixture consisting of an alkene and an oxygen-containing gas which does not require the presence of an organic carboxylic acid in the initial reaction mixture and, more specifically, for the preparation of vinyl acetate from ethylene and oxygen in the absence of acetic acid in the initial feed mixture. The process comprises contacting a gaseous feed comprising an alkene and an oxygen-containing gas with a catalyst comprising a palladium—or platinum—group metal or metal compound supported on alumina to obtain a reaction product mixture containing the unsaturated organic ester, the catalysts preferably being in sequence. The disclosure does not mention the use of mixed hydrocarbon feedstocks, the production of water and its removal, the recovery of acetic acid, or indeed any details of the various items of plant employed or their inter-relationship.

Research Disclosure, June 1992, page 446, discloses a process for the production of an acetic acid-containing product from ethane and/or ethylene which comprises:

(i) reacting ethane and/or ethylene with oxygen in an oxidation stage to produce an acetic acid-containing reaction product mixture containing, in addition to the acetic acid, unreacted ethane and ethylene and/or unreacted ethylene and carbon monoxide, optionally together with carbon dioxide and water;

(ii) subjecting the reaction product mixture with or without separating the acetic acid to an oxidation in which the carbon monoxide is selectively oxidised to carbon dioxide in the presence of the unreacted ethane and ethylene, and/or unreacted ethylene;

(iii) removing the carbon dioxide from the mixture; and (iv) recycling the unreacted ethane optionally together with the ethylene, and/or the unreacted ethylene to the ethane and/or ethylene oxidation stage.

In an embodiment of this invention reaction product from step (ii) comprising acetic acid, unreacted ethane (if present) and ethylene is passed with or without carbon dioxide and water removal to a reactor having a suitable catalyst for the production of ethyl acetate or, with addition of oxygen, for the production of vinyl acetate. There is no mention in this disclosure of the recovery of both acetic acid and vinyl acetate, nor of the role of water.

GB-A-1209727 discloses a process for preparing vinyl acetate by the catalytic oxidation of ethylene in the presence of acetic acid, which avoids the accumulation of impurities in the recycled gases and at the same time supplies the necessary acetic acid for preparing the vinyl acetate, the process being essentially characterised by the steps of drawing a convenient fraction of the recycled gases from the reactor in which the vinyl acetate is formed, catalytically oxidising the ethylene contained in said fraction to acetic acid with the aid of gaseous oxygen and supplying the acetic acid formed to the reactor in which the vinyl acetate is formed, the conditions being such that the content of by-products in the recycled gases is kept below 20% by volume, and the amount of acetic acid formed is sufficient to replace the acetic acid consumed in the preparation of vinyl acetate. No mention is made of the use of mixed hydrocarbon feedstocks, nor of recovering both acetic acid and vinyl acetate as products, nor of co-produced water and its role in the process.

There is a need for an integrated process capable of producing at least one of the products acetic acid and vinyl acetate.

Accordingly the present invention provides an integrated process for the production of acetic acid and/or vinyl acetate which comprises the steps:—

(a) contacting in a first reaction zone a gaseous feedstock comprising ethylene and/or ethane, and optionally steam, with a molecular oxygen-containing gas in the presence of a catalyst active for the oxidation of ethylene to acetic acid and/or ethane to acetic acid and ethylene to produce a first product stream comprising acetic acid, water and ethylene (either as unreacted ethylene and/or as co-produced ethylene), and optionally ethane, carbon monoxide, carbon dioxide and/or nitrogen;

(b) contacting in a second reaction zone in the presence or absence of additional ethylene and/or acetic acid at least a portion of the first gaseous product stream comprising at least acetic acid and ethylene and optionally also one or more of water, ethane, carbon monoxide, carbon dioxide and/or nitrogen with a molecular oxygen-containing gas in the presence of a catalyst active for the production of vinyl acetate to produce a second product stream comprising vinyl acetate, water, acetic acid and optionally ethylene;

(c) separating the product stream from step (b) by distillation into an overhead azeotrope fraction comprising vinyl acetate and water and a base fraction comprising acetic acid;

(d) either (i) recovering acetic acid from the base fraction separated in step (c) and optionally recycling the azeotrope fraction separated in step (c) after partial or complete separation of the water therefrom to step (c), or (ii) recovering vinyl acetate from the azeotrope fraction separated in step (c) and optionally recycling the base fraction separated in step (c) to step (b), or (iii) recovering acetic acid from the base fraction separated in step (c) and recovering vinyl acetate from the overhead azeotrope fraction recovered in step (c).

The process of the combination of steps (a) to (c) and (d) (i) may be considered as a process for the production of acetic acid by the oxidation of an ethylene and/or ethane feedstock in which the co-produced or added water is advantageously removed by distillation as a vinyl acetate/water azeotrope, leaving a substantially dried acetic acid product, the vinyl acetate used in the azeotrope distillation being provided by reacting a sufficient portion of the acetic acid produced by the oxidation with ethylene (either present as unreacted ethylene or as ethylene formed by oxidation of ethane) and molecular oxygen-containing gas.

The process of the combination of steps (a) to (c) and (d)(ii) may be considered as an integrated process for the production of vinyl acetate from ethylene and/or ethane via the intermediate formation of acetic acid, the process having the following advantages over a process with entirely separate acetic acid production:—

(i) insofar as a mixture of ethylene and ethane is used as the feedstock it facilitates the use of cracker off-gases or a partially purified ethylene/ethane stream which might otherwise be flared or require to be further purified. The purge of inert hydrocarbons, for example ethane, is either removed or reduced because they can be oxidised in the integrated process;

(ii) water co-produced with acetic acid in the oxidation reaction instead of being removed can pass with the acetic acid to the vinyl acetate production step. Thereafter it (the water) is advantageously separated by azeotroping with the vinyl acetate for distillative removal;

(iii) Infrastructures, utilities, and other features can be combined, for example only a single feed gas compressor and off-gas scrubbing system is required whereas separate acetic acid and vinyl acetate processes each require their own feed gas compressor and off-gas scrubbing system;

(iv) reduced intermediate storage requirements are needed as compared to two separate processes;

Advantages (iii) and (iv) lead to reduced capital and operating costs.

(v) it allows for heat integration; thus the ethylene/acetic acid from the first stage may be passed to the second stage at the required elevated temperature and with the acetic acid in vapour form without the need for heat input to vaporise the acetic acid, as is required with separate acetic acid and vinyl acetate processes.

The process of the combination of steps (a) to (c) and (d) (iii) may be considered as an integrated process for the production of acetic acid and vinyl acetate in any predetermined proportions. This in itself is an advantage since both acetic acid and vinyl acetate are world scale industrial products, the relative proportions of which can be adjusted by the process of the invention to accommodate prevailing market needs. Moreover, only acetic acid recovered as a product need be dried. This is a major advantage when it is considered that about half the current world production of acetic acid is utilised in vinyl acetate production.

In a first reaction zone a gaseous feedstock comprising ethylene and/or ethane is contacted with a molecular oxygen-containing gas in the presence of a catalyst active for the oxidation of ethylene to acetic acid and/or ethane to acetic acid and ethylene to produce a first product stream comprising acetic acid, water and ethylene (step (a)).

The catalyst active for the oxidation of ethylene to acetic acid, and/or ethane to acetic acid and ethylene may comprise any suitable catalyst known in the art, for example, as described in U.S. Pat. No. 5,304,678, U.S. Pat. No. 5,300,682, EP 0 407 091, EP 0 620 205, EP 0 294 845 and JP 06293695-A.

U.S. Pat. No. 5,304,678 describes a solid catalyst active for the oxidation of ethylene with molecular oxygen to form acetic acid, the catalyst containing the elements and proportions indicated by the empirical formula:

$$Pd_aM_bTiP_cO_x$$

where

M is selected from Cd, Au, Zn, Tl, alkali metals and alkaline earth metals, a is from 0.0005 to 0.2, b is from zero to 3a, c is from 0.5 to 2.5, and x is a value sufficient to satisfy the valence requirements of the other elements present, and wherein such catalyst contains crystalline $TiP_2O_7$.

U.S. Pat. No. 5,300,682 describes a solid catalyst active for the oxidation of ethane to form acetic acid and ethylene, the catalyst having the elements and relative atomic proportions indicated by the empirical formula:

$$VP_aM_bO_x$$

where M is one or more optional element selected from Co, Cu, Re, Fe, Ni, Nb, Cr, W, U, Ta, Ti, Zr, Zn, Hf, Mn, Pt, Pd, Sn, Sb, Bi, Ce, As, Ag, and Au, wherein a is 0.5 to 3, b is 0 to 1, and x is a number determined by the valence requirements of the other elements in the catalyst and wherein the catalyst contains crystalline vanadyl pyrophosphate, $(VO)_2P_2O_7$.

EP 0 407 091 describes a catalyst active for the oxidation of gaseous ethane and/or ethylene to form ethylene and/or acetic acid which catalyst comprises the elements A, X and Y in combination with oxygen, the gram-atom ratios of the elements A:X:Y being a:b:c, wherein $A = Mo_d Re_e W_f$, X=Cr, Mn, Nb, Ta, Ti, V and/or W, and preferably Mn, Nb, V and/or W, Y=Bi, Ce, Co, Cu, Fe, K, Mg, Ni, P, Pb, Sb, Si, Sn, Tl and/or U, and preferably Sb, Ce and/or U, a=1, b=0 to 2, preferably 0.05 to 1.0, c=0 to 2, preferably 0.001 to 1.0, and more preferably 0.05 to 1.0 with the proviso that the total value of c for Co, Ni and/or Fe is less than 0.5, d+e+f=a, d is either zero or greater than zero, e is greater than zero, and f is either zero or greater than zero.

EP 0 620 205 describes a catalyst active for producing acetic acid from ethylene and oxygen which catalyst comprises (a) metallic Pd and (b) at least one member selected from the group consisting of heteropoly-acids and their salts and optionally (c) at least one member selected from the group consisting of metallic elements of Groups 1B, 4B, 5B and 6B of the Periodic Table of Elements. The heteropoly-acids may contain one hetero-atom and one or more poly-atoms. The hetero-atom may preferably be selected from the group consisting of phosphorus, silicon, boron, aluminium, germanium, titanium, zirconium, cerium, cobalt, chromium and sulphur, and the poly-atoms may preferably be selected from the group consisting of molybdenum, tungsten, vanadium, niobium and tantalum. Component (c) may preferably be selected from copper, silver, tin, lead, antimony, bismuth, selenium and tellurium.

EP 0 294 845 describes a catalyst active for the oxidation of ethane to acetic acid and ethylene (as a by-product) and/or the oxidation of ethylene to acetic acid comprising at least two different catalyst entities. The first catalyst entity is a calcined ethane oxidation catalyst of formula:

in which the metal elements are in combination with oxygen in the form of various oxides. In this formula Z can be nothing or one or more of Li, Na, Be, Mg, Ca, Sr, Ba, Zn, Cd, Hg, Sc, Y, La, Ce, Al, Tl, Ti, Zr, Hf, Pb, Nb, Ta, As, Sb, Bi, Cr, W, U, Te, Fe, Co, Ni, and x is equal to 0.5 to 0.9, y is equal to 0.1 to 0.4 and z is equal to 0 to 1. The second catalyst entity is an ethylene hydration catalyst and/or an ethylene oxidation catalyst and includes one or more of the following classifications:

(i) a molecular sieve catalyst such as a zeolite Y, or silicate or an aluminophosphate or a metal aluminophosphate;

(ii) a palladium-containing oxide catalyst;

(iii) a tungsten-phosphorus-containing oxide catalyst;

(iv) a tin-molybdenum-containing oxide catalyst.

JP 06293695-A describes the oxidation of ethylene to acetic acid in the presence of a supported palladium catalyst containing one or more metals selected from chromium, vanadium, molybdenum and tungsten.

The catalyst active for the oxidation of ethylene and/or ethane may be used supported or unsupported. Examples of suitable supports include silica, diatomaceous earth, montmorillonite, alumina, silica alumina, zirconia, titania, silicon carbide, activated carbon, and mixtures thereof. The catalyst active for the oxidation of ethylene and/or ethane may be used in the form of a fixed or fluidised bed.

The molecular oxygen-containing gas used in the first reaction zone may be air or a gas richer or poorer in molecular oxygen than air. A suitable gas may be, for example, oxygen diluted with a suitable diluent, for example nitrogen or carbon dioxide. Preferably the molecular oxygen-containing gas is oxygen. Preferably, the molecular oxygen-containing gas is fed to the first reaction zone independently from the ethylene and/or ethane feedstock.

The ethylene and/or ethane feedstock of step (a) of the process of the present invention may be substantially pure or may be admixed with one or more of nitrogen, methane, carbon dioxide, hydrogen, and low levels of C3/C4 alkenes/alkanes.

It is preferred to feed water (steam) to the first reaction zone along with the ethylene and/or ethane feedstock and molecular oxygen-containing gas, because this can improve selectivity to acetic acid. The amount of steam fed to step (a) is suitably in the range greater than 0 to 50 mol %, preferably 10 to 30 mol %.

The gaseous feedstock of step (a) of the process of the present invention (ethylene and/or ethane) together with a molecular oxygen-containing gas is preferably passed through the catalyst at a gas hourly space velocity (GHSV) of 1000–10,000 $hr^{-1}$.

Step (a) of the process of the present invention may suitably be carried out at a temperature in the range from 100 to 400° C., typically in the range 140 to 210° C.

Step (a) of the process of the present invention may suitably be carried out at atmospheric or superatmospheric pressure, for example in the range from 80 to 400 psig.

Typically, ethylene conversions in the range 5 to 99% may be achieved in step (a) of the process of the present invention.

Typically, oxygen conversions in the range 30 to 100% may be achieved in step (a) of the process of the present invention.

In step (a) of the process of the present invention, the catalyst suitably has a productivity (STY) in the range 100 to 10000 grains of acetic acid per hour per liter of catalyst.

Depending upon the nature of the catalyst used in the second stage, it is desirable that the first gaseous product stream has a low concentration of carbon monoxide by-product as this may have an adverse effect on some catalysts for the production of vinyl acetate. Using such catalysts, with ethylene feedstock it is preferred to use a catalyst in the first reactor that gives negligible carbon monoxide by-product such as that described in EP-A-0620205. For ethane or ethylene feed, an additional catalyst component in the first reaction zone may be used to oxidise carbon monoxide to carbon dioxide. This may be present in the catalyst or in a secondary bed.

The gaseous product stream from step (a) comprises acetic acid, ethylene and water, and may contain ethane, oxygen, nitrogen and the by-products, acetaldehyde, carbon monoxide and carbon dioxide Acetaldehyde and carbon monoxide will be converted by the molecular oxygen-containing gas to produce acetic acid and carbon dioxide respectively, either in the second reaction zone or, after recycling, in the first reaction zone. Ethylene is present in the gaseous product stream of step (a) either as unconverted reactant if ethylene is present in the feedstock and/or as oxidation product if ethane is present in the feedstock.

The gaseous product from step (a) may be fed directly to the second reaction zone of step (b) together with optionally additional molecular oxygen-containing gas, optionally additional ethylene and optionally additional acetic acid. Acetic acid co-product may be optionally recovered from the gaseous product from step (a).

The catalyst active for the production of vinyl acetate which is used in step (b) of the process of the present invention may comprise any suitable catalyst known in the art, for example, as described in GB 1 559 540 and U.S. Pat. No. 5,185,308.

GB 1 559 540 describes a catalyst active for the preparation of vinyl acetate by the reaction of ethylene, acetic acid and oxygen, the catalyst consisting essentially of:

(1) a catalyst support having a particle diameter of from 3 to 7 mm and a pore volume of from 0.2 to 1.5 ml/g, a 10% by weight water suspension of the catalyst support having a pH from 3.0 to 9.0, (2) a palladium-gold alloy distributed in a surface layer of the catalyst support, the surface layer extending less than 0.5 mm from the surface of the support, the palladium in the alloy being present in an amount of from 1.5 to 5.0 grains per liter of catalyst, and the gold being present in an amount of from 0.5 to 2.25 grams per liter of catalyst, and (3) from 5 to 60 grams per liter of catalyst of alkali metal acetate.

U.S. Pat. No. 5,185,308 describes a shell impregnated catalyst active for the production of vinyl acetate from ethylene, acetic acid and an oxygen containing gas, the catalyst consisting essentially of:

(1) a catalyst support having a particle diameter from about 3 to about 7 mm and a pore volume of 0.2 to 1.5 ml per gram, (2) palladium and gold distributed in the outermost 1.0 mm thick layer of the catalyst support particles, and (3) from about 3.5 to about 9.5% by weight of potassium acetate wherein the gold to palladium weight ratio in said catalyst is in the range 0.6 to 1.25.

An advantage of using a palladium-containing catalyst is that any carbon monoxide produced in the first reaction zone will be consumed in the presence of oxygen and the palladium-containing catalyst in the second reaction zone, thereby eliminating the need for a separate carbon monoxide removal reactor.

Typically, step (b) of the process of the present invention is carried out heterogeneously with the reactants being present in the gas phase.

The ethylene reactant used in step (b) of the process of the present invention may comprise ethylene product from step (a), unreacted ethylene feedstock from step (a) or additional ethylene reactant.

The molecular oxygen-containing gas used in step (b) of the process of the present invention may comprise unreacted molecular oxygen-containing gas from step (a) and/or additional molecular oxygen-containing gas. Preferably, at least some of the molecular oxygen-containing gas is fed independently to the second reaction zone from the acetic acid and ethylene reactants.

The acetic acid, ethylene and molecular oxygen-containing gas which are reacted in step (b) of the process of the present invention are preferably passed through the catalyst at a gas hourly space velocity (GHSV) in the range 1000–10000 $hr^{-1}$.

Step (b) of the process of the present invention may suitably be carried out at a temperature in the range from 140 to 200° C.

Step (b) of the process of the present invention may suitably be carried out at a pressure in the range 50 to 300 psig.

Step (b) can be carried out in either a fixed or a fluidised bed.

Acetic acid conversions in the range 5 to 50% may be achieved in step (b) of the process of the present invention.

Oxygen conversions in the range 20 to 100% may be achieved in step (b) of the process of the present invention.

Ethylene conversions in the range 5 to 1000% may be achieved in step (b) of the process of the present invention.

In step (b) of the process of the present invention, the catalyst suitably has a productivity (STY) in the range 300 to 10000 grams of vinyl acetate per hour per liter of catalyst, but >10000 grams of vinyl acetate per hour per liter of catalyst is also suitable.

The second product stream from step (b) of the process comprises vinyl acetate, water and acetic acid and optionally also unreacted ethylene, ethane, acetaldehyde, nitrogen, carbon monoxide and carbon dioxide. Intermediate between step (b) and step (c) of the process of the invention it is preferred to remove ethylene, and ethane, acetaldehyde, carbon monoxide and carbon dioxide, if any, from the second product stream, suitably as an overhead gaseous fraction from a scrubbing column, in which a liquid fraction comprising vinyl acetate, water and acetic acid is removed from the base.

The second product stream from step (b) comprising vinyl acetate, water and acetic acid, with or without the intermediate scrubbing step, is separated in step (c) by distillation into an overhead azeotrope fraction comprising vinyl acetate and water and a base fraction comprising acetic acid.

In step (d) alternative (i) of the process of the invention acetic acid is recovered from the base fraction separated in step (c). The recovered acetic acid may be further purified if desired, in known manner, for example by distillation. The azeotrope fraction removed as an overhead fraction is preferably recycled, with complete or partial separation of the water therefrom, by for example cooling and decantation, to step (c) of the process.

In step (d) alternative (ii) vinyl acetate is recovered from the azeotrope fraction separated in step (c), suitably for example by decantation. The recovered vinyl acetate may, if desired, be further purified in known manner. The base fraction comprising acetic acid separated in step (c) is preferably recycled, with or preferably without further purification, to step (b) of the process.

In step (d) alternative (iii) acetic acid is recovered from the base fraction separated in step (c) and vinyl acetate is recovered from the overhead azeotrope fraction recovered in step (c). Both the acetic acid and the vinyl acetate may be further purified in known manner if desired. The relative yield of acetic acid to vinyl acetate may be adjusted to any pre-determined value.

The ratio of overall yields of acetic acid: vinyl acetate produced in the process may be in the range 0:100 to 100:0, for example 0:100 to 70:30. The ratio of 0:100 represents alternative (d)(ii) of the process in which acetic acid is all converted to vinyl acetate. The ratio 100:0 represents alternative (d)(i) of the process in which vinyl acetate is only made in sufficient amounts to effect the azeotropic distillation and none is recovered. All the ratios in between these two extremes represent alternative (d)(iii) of the process in which both acetic acid and vinyl acetate are recovered.

The overall yield ratio may be varied in a number of ways including independently adjusting the reactant ratios and/or reaction conditions of step (a) and/or step (b) of the process, for example by independently adjusting the oxygen concentration(s) and/or the reaction temperatures and pressures.

BRIEF DESCRIPTION OF THE DRAWINGS

The process of the present invention will now be illustrated by example with reference to FIG. 1 which represents in schematic form apparatus for use in the process of the present invention.

The apparatus comprises a first reaction zone (1), an optional heat exchanger (2), a second reaction zone (3), a heat exchanger (9), a scrubber column (4), a first distillation column (5), a decanter (6), an optional vaporiser (7) and an optional second distillation column (8).

Figure 1:
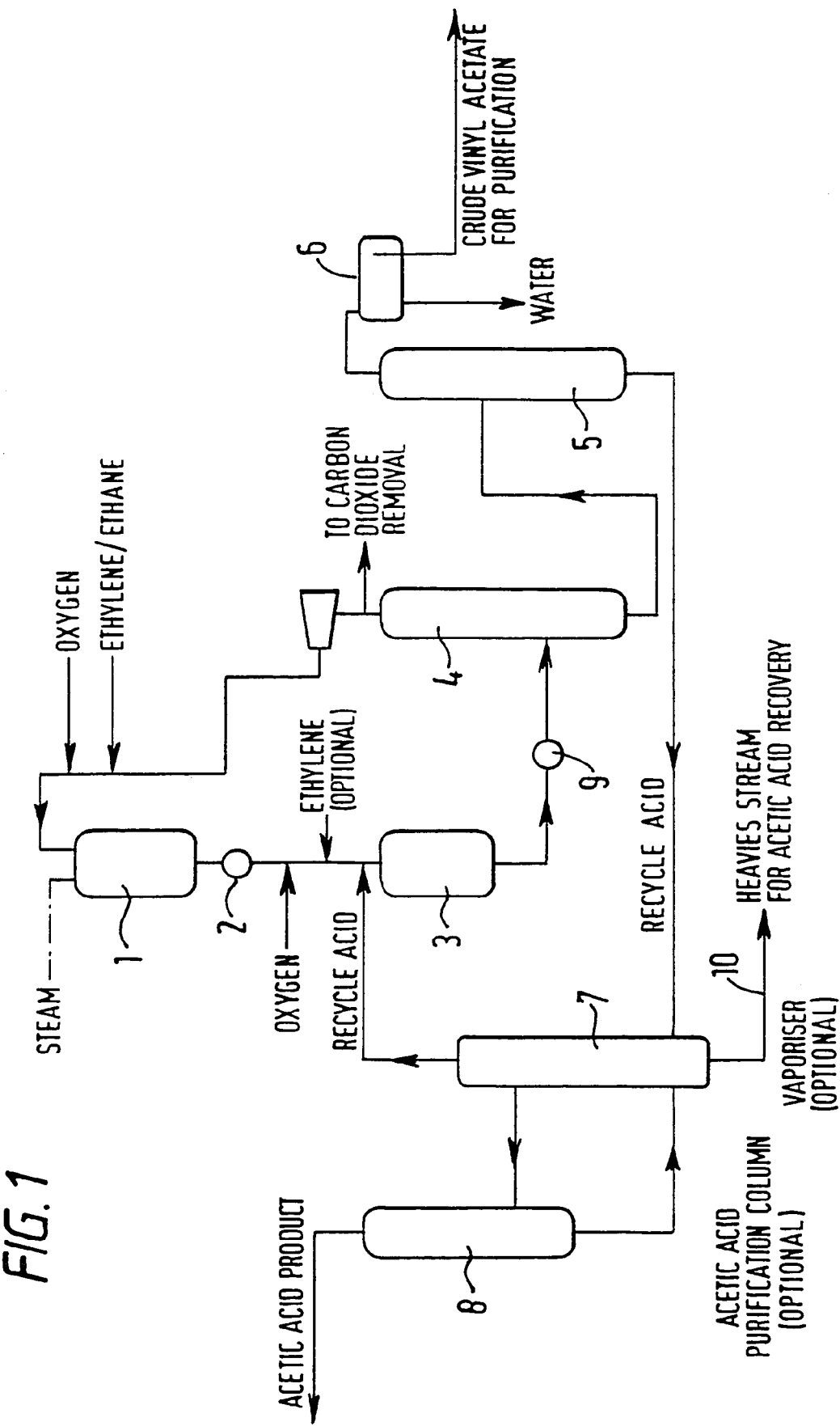

In use, a molecular oxygen-containing gas, optional steam and a gaseous feedstock comprising ethylene and/or ethane are fed to the first reaction zone (1) which contains a catalyst active for the oxidation of the ethylene to form acetic acid, and/or the oxidation of ethane to form acetic acid and ethylene. Depending on the scale of the process, the first reaction zone (1) may comprise either a single reactor or several reactors in parallel or series. A first gaseous product stream comprising acetic acid, unreacted feedstock, optionally unconsumed molecular oxygen-containing gas and water together with carbon monoxide, carbon dioxide, inerts and acetaldehyde by-products is withdrawn from the first reaction zone (1) and is fed to the second reaction zone (3), via optional heat exchanger (2) which allows adjustment of the temperature of the feed to the second reaction zone (3). It is envisaged that if no heat exchanger (2) is required it may be possible to have the first and second reaction zones in the same vessel. Additional molecular oxygen-containing gas and/or ethylene and/or acetic acid recycle may be mixed with the product stream withdrawn from the first reaction zone (1). In the second reaction zone (3) acetic acid and ethylene are contacted with molecular oxygen-containing gas in the presence of a catalyst active for the production of vinyl acetate. Depending on the scale of the process, the second reaction zone (3) may comprise either a single reactor or several reactors in parallel or in series. A product stream comprising vinyl acetate, water, optionally ethane, gaseous by-products and unreacted acetic acid and ethylene is withdrawn from the second reaction zone (3) and is fed, via heat exchanger (9), to the scrubber column (4) where a gaseous stream comprising ethylene, and optionally ethane together with acetaldehyde, inerts, carbon monoxide and carbon dioxide by-products is withdrawn overhead and is recycled to the first reaction zone (1). A liquid stream comprising vinyl acetate, water, unreacted acetic acid and heavy organic by-products is withdrawn from the base of the scrubber column (4) and is fed to the first distillation column (5). In the first distillation column (5) vinyl acetate and water is removed as an azeotrope and acetic acid, and the heavy organic by-products are removed as a bleed from the base of the first distillation column (5). The water in the overhead stream from the first distillation column (5) is separated from the vinyl acetate in a decanter (6) and a vinyl acetate product stream removed from decanter (6) is purified by conventional means known in the art. The acetic acid-containing bleed stream removed from the base of the first distillation column (5) may be fed to the optional vaporiser (7) wherein acetic acid is separated as a vapour fraction comprising acetic acid from a heavy ends liquid fraction (10) comprising acetic acid and heavy organic by-products. Acetic acid may be recovered from the heavy ends liquid fraction by conventional means known in the art. The vapour fraction from the optional vaporiser (7) may be recycled to the reaction zone (3). A portion of the acetic acid-containing bleed stream removed from the base of the first distillation zone (5) and/or a portion of the vapour fraction from the optional vaporiser (7) may be fed to a second distillation column (8). An acetic acid product stream is optionally withdrawn overhead from the second distillation column (8).

Carbon dioxide by-product can be removed from a bleed from the top of the scrubber column (4) for example by absorption by potassium carbonate/bicarbonate mixtures.

Items (2) to (7) may be units of a conventional vinyl acetate manufacturing plant which may provide benefits of reduced capital installation costs.

The invention claimed is:

1. An apparatus for performing an integrated process for the production of acetic acid and/or vinyl acetate, which comprises:

a first reaction zone for contacting a gaseous feedstock comprising ethylene and/or ethane and optionally steam with a molecular oxygen-containing gas in the presence of a catalyst active for the oxidation of ethylene to acetic acid and/or ethane to acetic acid and ethylene to produce a first gaseous product stream comprising acetic acid, water and ethylene, either as unreacted ethylene and/or as co-produced ethylene, and optionally also ethane, carbon monoxide, carbon dioxide and/or nitrogen;

a second reaction zone for contacting in the presence or absence of additional ethylene and/or acetic acid, at least a portion of the first gaseous product stream comprising at least acetic acid and ethylene and optionally also one or more of water, ethane, carbon monoxide, carbon dioxide and/or nitrogen with a molecular oxygen-containing gas in the presence of a catalyst active for the production of vinyl acetate to produce a second product stream comprising vinyl acetate, water, acetic acid and optionally ethylene, said contacting in said second reaction zone being carried out heterogeneously with the ethylene, acetic acid and molecular oxygen-containing gas being present in the gas phase;

a separator for separating the product stream from step (b) by distillation into an overhead azeotrope fraction comprising vinyl acetate and water and a base fraction comprising acetic acid;

a first distillation column through which said base fraction is passed;

a decanter through which an overhead stream from said first distillation column is passed.

2. An apparatus according to claim 1, wherein said first reaction zone comprises a single reactor.

3. An apparatus according to claim 1, wherein said first reaction zone comprises several reactors in parallel or in series.

4. An apparatus according to claim 1, wherein a heat exchanger is provided between said first reaction zone and said second reaction zone.

5. An apparatus according to claim 1, wherein said first and second reaction zones are contained within the same vessel.

6. An apparatus according to claim 1, wherein said second reaction zone comprises a single reactor.

7. An apparatus according to claim 1, wherein said second reaction zone comprises several reactors in parallel or in series.

8. An apparatus according to claim 1, wherein a heat exchanger is provided between said second reaction zone and said separator.

9. An apparatus according to claim 1, and further comprising a vaporizer through which base stream from said first distillation column is passed.

10. An apparatus according to claim 9, and further comprising a second distillation column through which a vapor fraction from said vaporizer is passed.

11. An apparatus according to claim 1, wherein said first reaction zone comprises a fixed bed.

12. An apparatus according to claim 1, wherein said first reaction zone comprises a fluidized bed.

13. An apparatus according to claim 1, wherein said second reaction zone comprises a fixed bed.

14. An apparatus according to claim 1, wherein said second reaction zone comprises a fluidized bed.

* * * * *

UNITED STATES PATENT AND TRADEMARK OFFICE
CERTIFICATE OF CORRECTION

| | | |
|---|---|---|
| PATENT NO. | : 7,189,377 B1 | Page 1 of 1 |
| APPLICATION NO. | : 09/626157 | |
| DATED | : March 13, 2007 | |
| INVENTOR(S) | : Jobson et al. | |

It is certified that error appears in the above-identified patent and that said Letters Patent is hereby corrected as shown below:

Title page of the patent Item (60) "Related U.S. Application Data", at line 5, please delete "Feb. 5, 1997" and insert --Aug. 5, 1997.--

Signed and Sealed this

First Day of May, 2007

JON W. DUDAS
*Director of the United States Patent and Trademark Office*